(12) United States Patent
LeGrow et al.

(10) Patent No.: US 6,489,274 B1
(45) Date of Patent: Dec. 3, 2002

(54) LIQUID RINSE-OFF COMPOSITIONS FOR PERSONAL CARE COMPRISING A TRIMETHYL-SILYLALKYLSILSESQUIOXANE

(75) Inventors: Gary E. LeGrow, Newberry, FL (US); W. Leonard Terry, Jr., Gainsville, FL (US); Ray Figueroa, Hollywood, FL (US); Peter Klug, Grossostheim (DE); Angelika Turowski, Kelkheim (DE)

(73) Assignee: Clariant International Ltd., Muttenz (CH)

( * ) Notice: Subject to any disclaimer, the term of this patent is extended or adjusted under 35 U.S.C. 154(b) by 0 days.

(21) Appl. No.: 10/002,057
(22) Filed: Oct. 24, 2001
(51) Int. Cl.⁷ .................................. C11D 9/36
(52) U.S. Cl. ............... 510/122; 510/119; 510/130; 510/466
(58) Field of Search ............... 510/119, 122, 510/130, 466

(56) References Cited

U.S. PATENT DOCUMENTS

| 5,923,231 A | 7/1999 | Ohkubo et al. |
| 6,143,309 A | * 11/2000 | Legrow et al. ............. 424/401 |

OTHER PUBLICATIONS

U.S. application No. 10/001,293, filed Oct. 24, 2001.
U.S. application No. 10/002,709, filed Oct. 24, 2001.
U.S. application No. 10/002,710, filed Oct. 24, 2001.

* cited by examiner

Primary Examiner—Charles Boyer
(74) Attorney, Agent, or Firm—Richard P. Silverman

(57) ABSTRACT

This invention relates to liquid rinse-off compositions for personal care comprising trimethylsilylalkylsilsesquioxanes, particularly trimethylsilyl-n-octylsilsesquioxanes (Caprylyl Trimethicones). Preferably the rinse-off compositions are shampoos containing pearlescent and/or opacifying agents.

16 Claims, No Drawings

LIQUID RINSE-OFF COMPOSITIONS FOR PERSONAL CARE COMPRISING A TRIMETHYL-SILYLALKYLSILSESQUIOXANE

FIELD OF THE INVENTION

This invention relates to liquid rinse-off compositions for personal care comprising high purity trimethylsilyl-alkylsilsesquioxanes, particularly trimethylsilyl-n-octylsilsesquioxanes (caprylyl trimethicones). Said rinse-off compositions provide excellent rinse feel and skin mildness. They are suitable for simultanously cleansing and conditioning of the skin and/or the hair and can be used in the form of foam bath preparations, shower products, skin cleansers, hand cleansers, face cleansers and body cleansers, shampoos etc.

BACKGROUND OF THE PRESENT INVENTION

In recent years there has been a fast development in the field of skin and hair care. Improved products, according to the actual trends, were offered to the customers. The development is focused on rinse-off formulations which guarantee effective cleansing together with other supplemental benefits such as improved sensory, conditioning, gloss and sheen properties. The patent literature describes several ways to achieve the above-mentioned goals. Among others, silicones are found in many personal care products including topical skincare products, 2-in-1 hair shampoo-conditioners, color cosmetics (mascara, lipstick), anti-perspirants and deodorants. Dimethylsilicones, both linear and cyclic, are proposed to improve the sensory properties. Unfortunately said dimethylsilicones are generally not compatible with water. Also they show little compatibility with many organic materials used in cosmetic formulations. Phenyl trimethicones are another class of silicones often used in cosmetic industry.

In recent years considerable research concerning the ultimate fate of organosilicones (atmosphere, lakes and rivers rivers) has been carried out. For example phenyl substituents are oxidized and/or homolytically cleaved off to form benzene and/or phenol. Both are pollutants of the environment.

DESCRIPTION OF THE PRESENT INVENTION

We have now found that trimethylsilylalkylsilsesquioxanes are particularly suitable for use in formulating liquid rinse-off compositions for personal care.

Surprisingly it has been found that said trimethylsilyl-alkylsilsesquioxanes are particularly useful for formulating shampoos additionally containing insoluble components, preferably peariescing and/or opacifying agents. Trimethylsilyl-octylsilsesquioxanes (caprylyl trimethicones) can be stabilized over a long period of time and over broad temperature ranges in the presence of pearlizing or opacifying agents. Said trimethylsilyl-alkylsilsesquioxanes considerably increase the gloss and sheen of the hair and also considerably increase the emolliency and water repellency of the skin. During the application they provide enhanced spreadability, lubricity and reduced tackiness. Advantageously said trimethylsilyl-alkylsilsesquioxanes are environmentally friendly and show excellent compatibility with many organic materials used in cosmetic formulations.

Therefore, the present invention provides liquid rinse-off compositions for personal care comprising at least 0.1% by weight of at least one trimethyl-silylalkylsilsesquioxane of formula (1)

$$Me_3SiO-[Si(R)(OSiMe_3)O]_x-SiMe_3 \quad (1)$$

wherein Me is methyl, R is a straight or branched alkyl group having from 6 to 18 carbon atoms and x is a number from 1 to 10, at least 2% by weight of water-soluble surfactants and, at least 50% by weight of water.

R in formula (1) has preferably from 6 to 14 carbon atoms. Particularly preferred as trimethyl-silylalkylsilsesquioxanes of formula (1) are trimethylsilyl-n-octylsilsequioxanes (caprylyl trimethicones) wherein R is an n-octyl group —$C_8H_{17}$. Preferably the trimethyl-silylalkylsilsesquioxanes are compounds according to formula (1) wherein x is a number from 1 to 6. More preferred x is equal to 1, 2, 3 and/or 4.

Surprisingly it has been found that trimethylsilylalkyl-silsesquioxane of formula (1), which are substantially free of alkoxysilanes, chlorosilanes, silanol functionalities and organic and/or inorganic compounds, are particularly useful for the present invention. More preferred the trimethylsilylalkyl-silsesquioxanes of formula (1) contain less than 3% by weight, more preferred less than 1% by weight, of alkoxysilanes, chlorosilanes, silanol functionalities and organic and/or inorganic compounds. Such high purity trimethylsilylalkyl-silsesquioxanes of formula (1) can be prepared according to the process described in U.S. Pat. No. 5,932,231 by hydrolyzing a mixture of pure trimethyl-chlorosilane and pure alkyltrichlorosilane having from 6 to 18, preferably 6 to 14, carbon atoms with distilled water in an amount sufficient to produce an aqueous layer of less than about 25 weight percent hydrochloric acid, maintaining the temperature of the hydrolysis reaction mixture below about 90° C., to form a silicone intermediate; washing residual acid from the silicone reaction intermediate; and azeotropicallay removing water from the washed silicone intermediate to produce a dried silicone reaction intermediate; and trimethylsilylating the silanol groups in the dried silicone reaction intermediate with at least a stoichiometric amount of hexamethyldisiloxane in the presence of an acid catalyst.

All the embodiments of the process described in U.S. Pat. No. 5,932,231 are hereby incorporated by reference into the description of the present application.

Preferably the rinse-off compositions comprise from 0.1 to 5% by weight, more referred from 0.2 to 2.5% by weight, particularly preferred from 0.5 to 1.5% by weight, of trimethyl-silylalkylsilsesquioxanes of formula (1). It is an essential feature of the invention that the the rinse-off compositions comprise at least 2% by weight of water-soluble surfactants.

Preferably the rinse-off compositions comprise from 2 to 40% by weight, more preferred from 3 to 20% by weight, particularly preferred from 5 to 15% by weight, of water-soluble surfactants.

Said water-soluble surfactants can be selected from anionic, cationic, amphoteric, zwitterionic and/or nonionic surfactants. Preferably the rinse-off compositions contain mixtures of surfactants. Anionic surfactants are preferably present at levels from 0.1 to 20% by weight, more preferred from 0.1 to 15% by weight, particularly preferred from 1 to 10% by weight.

Cationic surfactants are preferably present at levels from 0.1 to 20% by weight, more preferred from 0.1 to 15% by weight, particularly preferred from 1 to 10% by weight.

Amphoteric surfactants are preferably present at levels from 0,1 to 20% by weight, more preferred from 1 to 8% by weight.

Zwitterionic surfactants are preferably present at levels from 0,1 to 20% by weight, more preferred from 0,1 to 10% by weight, particularly preferred from 1 to 8% by weight.

Nonionic surfactants are preferably present at levels from 0,1 to 20% by weight, more preferred from 1 to 8% by weight.

In a preferred embodiment the rinse-off compositions contain a mixture of anionic and zwitterionic and/or amphoteric surfactants.

The weight ratio of anionic surfactants to zwitterionic and/or amphoteric surfactants is preferably from 1:10 to 10:1, more prefered from 1:5 to 5:1, particularly preferred from 1:3 to 3:1.

In another preferred embodiment the rinse-off compositions contain anionic, zwitterionic and/or amphoteric surfactants together with at least one nonionic surfactant.

Preferred anionic surfactants are alkyl sulfates; ethoxylated alkyl sulfates, such as laureth-2-sulfate; sodium laureth-3 sulfate; ammonium laureth-3 sulfate, magnesium laureth-3,6 sulfate; salts of sulfuric acid esters; alkyl ethoxy carboxylates; alkyl glyceryl ether sulfonates; ethoxy ether sulfonates; methyl acyl taurates; fatty acyl glycinates; N-acyl glutamates; acyl isethionates; alkyl sulfosuccinates; alkyl ethoxysulphosuccinates; alpha-sulfonated fatty acids and salts and/or esters thereof; alkyl phosphate esters; ethoxylated alkyl phosphate esters; acyl sarcosinates; fatty acid/protein condensates; soaps (e.g. ammonium-, magnesium-, potassium-, sodium salts of lauric acid, myristic acid, palmitic acid); acyl aspartates; alkoxy cocamides; carboxylates; (ethoxylated)alkanolamide sulphosuccinates; ethoxylated alkyl citrate; sulphosuccinate; acyl ethylene diamine triacetates; alkylhydroxyethyl isethionates; acyl amide alkoxy sulfates; linear alkyl benzene sulfonates; paraffin sulfonates; alpha-olefin sulfonates; alkyl alkoxy sulfates; and mixtures thereof. Preferably the alkyl and acyl chain of such surfactants has from 6 to 22, more preferred from 12 to 18, particularly preferred from 12 to 14, carbon atoms.

Preferred amphoteric surfactants are $R_1CON(R_3)CH_2CH_2N(R_2)CH_2CO_2M$, wherein $R_1$ is $(C_5-C_{22})$-alkyl or -alkenyl, $R_2$ is $CH_2CH_2OH$ or $CH_2CO_2M$ and M is H, an alkali metal, an alkaline earth metal, an ammonium- or alkanolammonium ion and $R_3$ is $CH_2CH_2OH$ or H; aminoalkanoates; iminodialkanoates; and/or iminopolyalkanoates.

More preferred are cocoamphocarboxypropionate, cocoamphocarboxy propionic acid, cocoamphoacetate, cocoamphodiacetate(cocoamphocarboxyglycinate), sodium lauroamphoacetate (lauroamphocarboxyglycinate), N-alkyl polytrimethylene, and carboxymethylamines.

Preferred zwitterionic surfactants are alkyl betaines of the formula $R_5R_6R_7N^+(CH_2)_nCO_2M$, and amido betaines of the formula $R_5CON(CH_2)_mNR_6R_7(CH_2)_nCO_2M$, wherein $R_5$ is $(C_5-C_{22})$-alkyl or -alkenyl, $R_6$ and $R_7$ are independently $(C_1-C_3)$-alkyl, M is H, an alkali metal, a alkaline earth metal, an ammonium- or an alkanolammonium ion and n and m are each numbers from 1 to 4. Preferred as betaine surfactant is cocoamidopropyl-dimethyl-carboxymethylbetaine.

Preferred nonionic surfactants are sucrose polyester surfactants, $(C_{10}-C_{18})$-alkyl polyglycosides and polyhydroxy fatty acid amides.

The rinse-off compositions may also comprise so-called additional surfactants. Preferred additional surfactants are alkylamido sultaines and amine oxides.

The rinse-off compositions comprise at least 50% by weight of water. Preferably they contain from 50 to 90% by weight, more preferred from 60 to 90% by weight of water.

Preferably the rinse-off compositions additionally comprise one or more polymeric cationic conditioning agents which are useful to provide desirable skin feel attributes.

Said conditioning agents are preferably present at levels from 0.01 to 5% by weight, more preferred from 0.01 to 3% by weight, particularly preferred from 0.01 to 2% by weight.

Suitable conditioning agents are guar gums, cationic polysaccharides, cationic homopolymers and copolymers derived from acrylic and/or methacrylic acid, cationic cellulose resins, quaternized ethyl cellulose ethers, cationic copolymers of dimethyldiallylammonium chloride and acrylamide and/or acrylic acid, cationic homopolymers of dimethyldiallylammonium chloride, copolymers of dimethyl aminoethylmethacrylate and acrylamide, acrylic acid/dimethyidiallylammonium chloride/acrylamide copolymers, quaternized vinyl pyrrolidone acrylate or methacrylate copolymers of amino alcohols, quaternized copolymers of vinyl pyrrolidone and dimethylaminoethylmethacrylamide, vinyl pyrrolidone/vinyl imidazolium methochloride copolymers and polyalkylene and ethoxypolyalkylene imines, terpolymers of acrylic acid, methacrylamidipropyl trimethyl ammonium chloride and methyl acrylate and mixtures thereof.

The rinse-off compositions may also comprise from 0.1% to 20% by weight, preferably from 1% to about 15% by weight, more preferred from 2% to 10% by weight, of oil derived nonionic surfactants or mixtures thereof.

Said oil derived nonionic surfactants are beneficial for the skin feel properties both during and after use. Suitable oil derived nonionic surfactants include water soluble vegetable and animal-derived emollients such as triglycerides with an inserted polyethylenglycol chain, ethoxylated mono- and di-glycerides, polyethoxylated lanolins and ethoxylated butter derivatives. Suitable ethoxylated oils and fats include polyethylenglycols, derivatives of glyceryl cocoate, glyceryl caproate, glyceryl caprylate, glyceryl tallowate, glyceryl plamate, glyceryl stearate, glyceryl laurate, glyceryl oleate, glyceryl ricinoleate and glyceryl fatty esters derived from triglycerides, such as palm oil, almond oil and corn oil, preferably glyceryl tallowate and glyceryl cocoate. Other suitable oil-derived nonionic surfactants include ethoxylated derivatives of almond oil, peanut oil, rice bran oil, wheat germ oil, linseed oil, jojobaoil, oil of apricot pits, walnuts, palm nuts, pstachio nuts, sesame seeds, rapeseed, cade oil, corn oil, peach pit oil, poppyseed oil, pine oil, castor oil, soybean oil, avocado oil, safflower oil, coconut oil, hazelnut oil, olive oil, grapseed oil, and sunflower seed oil.

The rinse-off compositions may additionally comprise lipophilic emulsifiers as skin care actives. Suitable lipohilic skin care actives include anionic food grade emulsifiers which comprise mixtures of diacids and monoglycerides (e.g. succinylated monoglycerides, monostearyl citrate, glyceryl monostearate diacetyl tartrate and mixtures thereof).

The rinse-off compositions may additionally comprise water-insoluble poly-alpha-olefin oils (e.g. polymers of butene, isoprene, terpene, styrene or isobutene).

The rinse-off compositions may additionally comprise hydrophobically modified silicones according to formula (2)

$$(R^1)_3SiO-[Si(R^2)(R^3)O]_x-[Si(R^2)(R^2)O]_y-OSi(R^1)_3 \qquad (2)$$

wherein $R^1$ is a $(C_1-C_{20})$-alkyl or phenyl group, $R^2$ is a $(C_1-C_4)$-alkyl or phenyl group, $R^3$ is a $(C_2-C_{25})$-alkyl or phenyl group, x is a number from 20 to 400, y is a number from 0 to 10 and x+y is a number from 30 to 400.

It should be noted that x and y are average polymerisation degrees and therefore the compositions generally contain silicones of different individual x and y values.

Other water-insoluble skin/hair care ingredients suitable for foaming compositions are liquid polyol carboxylic acid esters. Preferred liquid polyol polyesters comprise polyols (e.g. erythritol, xylitol, sorbitol, glucose, sucrose, particularly sugars or sugar alcohols, monosaccharides, e.g. xylose, arabinose, disaccharides) esterfied with at least four fatty acid groups.

The rinse-off compositions may additionally comprise auxiliary nonionic or anionic polymeric thickeners, particularly water-soluble polymeric materials having a molecular weight greater than about 20,000 g/mol. Preferred water-soluble polymeric materials form a substantially clear aqueous solution at concentrations of 1% by weight at 25° C. Examples of preferred water-soluble polymers are hydroxyethylcellulose, hydroxypropylcellulose, hydroxypropyl methylcellulose, polyethylene glycols, polyacrylamide, polyacrylic acid, polyvinyl alcohol, polyvinyl pyrrolidone and polysaccharide, such as guar gum, locust bean gum and xantham gum.

The rinse-off compositions optionally comprise so-called hydrotropes. Hydrotropes are materials capable to modify the viscosity and rheology profile of a non-dilute, water-soluble surfactant system. Suitable as hydrotropes are those well known in the art, including sodium xylene sulphonate, ammonium xylene sulphonate, sodium cumene sulphonate, short chain alkyl sulphate and mixtures thereof.

The hydrotrope may be present at levels from 0.01% to 5% by weight, preferably from 0.1% to 4% by weight, more preferred from 0.5% to 3% by weight.

Additionally the rinse-off compositions may comprise an insoluble perfume or cosmetic oil or wax or a mixture thereof at levels up to 10% by weight, preferably up to 3% by weight. Insoluble oil or wax means insoluble in the product matrix at a temperature of 25° C.

Suitable insoluble cosmetic oils and waxes can be selected from water-insoluble silicones including non-volatile polyalkyl and polyaryl siloxane gums and fluids, volatile cyclic polydimethylsiloxanes, polyalkoxylated silicones, amino and quaternary ammonium modified silcones, rigid cross-linked and reinforced silcones and mixtures thereof, ($C_1$–$C_{24}$)-esters of ($C_8$–$C_{30}$)-fatty acids such as isopropyl myristate, myristyl myristate and cetyl ricinoleate, ($C_8$–$C_{30}$) esters of benzoic acid, beeswax, saturated and unsaturated fatty alcohols such as behenyl alcohol, hydrocarbons such as mineral oils, petrolatum, squalane and squalene, fatty sorbitan esters, lanolin and oil-like lanolin derivatives, animal and vegetable triglycerides such as almond oil, peanut oil, wheat germ oil, rice bran oil, linseed oil, jojoba oil, oil of apricot pits, walnuts, palm nuts, pistachio nuts, sesame seeds, rapeseed, cade oil, corn oil, peach pit oil, poppyseed oil, pine oil, castor oil, soyabean oil, avocado oil, safflower oil, coconut oil, hazelnut oil, olive oil, grapeseed oil, sunflower seed oil, ($C_1$–$C_{24}$) esters of dimer and trimer acids such as diisopropyl dimerate, diisostearylmalate, diisostearyldimerate and triisostearyltrimerate.

The rinse-off compositions preferably have a viscosity of at least 500 cps, more preferred from 1,000 to 50,000 cps, particularly preferred from 1,000 to 30,000 cps, highly preferred from 1,000 to 15,000 cps.

The rinse-off compositions optionally include other hair or skin moisturizers which are soluble in the composition matrix. The preferred level of such moisturizers is from 0.5% to 20% by weight. Preferred moisturizer are selected from essential amino acid compounds naturally occurring in the stratum corneum of the skin and water-soluble nonpolyol nonocclusives and mixtures thereof.

More preferred nonocclusive moisturizers are squalane, sodium pyrrolidone carboxylic acid, D-panthenol, lactic acid, L-proline, guanidine, pyrrolidone, hydrolyzed protein and other collagen-derived proteins, aloe vera gel, acetamide MEA and lactamide MEA and mixtures thereof.

The rinse-off compositions may also comprise suspendind agents. The suspending agents serve to assist in suspending the water-insoluble oil and may give pearlescence to the product.

Suitable suspending agents include any long chain acyl derivative materials or mixtures thereof. Preferred suspending agents are ethylene glycol esters of fatty acids having from 16 to 22 carbon atoms. More preferred are ethylene glycol stearates, both mono- and distearate. Particularly preferred are distearates containing less than 7% by weight of monostearate.

Other suitable suspending agents are alkanol amides of fatty acids having from 16 to 22 carbon atoms, preferably from 16 to 18 carbon atoms. Preferred alkanol amides are stearic monoethanolamide, stearic diethanolamide, stearic monoisopropanolamide and stearic monoethanolamide stearate.

Also suitable suspending agents are alkyl-($C_{16}$–$C_{22}$)-dimethyl amine oxides such as stearyl dimethyl amino oxide and trihydroxystearin; copolymers based on acryl alkyl sulfonic acids and cyclic N-vinyl carboxylic acid amides respectively cyclic and linear N-vinyl carboxylic acid amides; comb-like, optionally grafted, acryloyl dimethyl taurate containing copolymers which may contain cationic charges, Si-, F- and/or P-atoms in their backbone or side chains.

Other suitable suspending agents include xantham gum, preferably in combination with long chain acyl derivatives, also carboxyvinyl polymers. Preferred among these polymers are copolymers of acrylic acid crosslinked with polyallylsucrose, carbomers, which are homopolymers of acrylic acid crosliked with an allyl ether of pentaerythrotol, an allyl ether of sucrose, or an allyl ether of propylene.

Other suitable suspending agents can be used in the shampoo compositions, including those that can impart a gel-like viscosity to the composition, such as a water soluble or colloidally water soluble polymers like cellulose ethers such as hydroxyethyl cellulose, and materials such as guar gum, polyvinyl alcohol, polyvinyl pyrrolidone, hydroxypropyl guar gum, starch and starch derivatives, and other thickeners, viscosity modifiers, gelling agents etc. Mixtures of these materials can also be used.

Other suitable suspending agents include N,N-dihydrocarbyl amido benzoic acid and soluble salts therof (e.g. Na, and K salts), particularly N,N-di(hydrogenated) ($C_{16}$–$C_{18}$) and tallow amido benzoic acid species of this family.

The suspending agents are preferably present at levels of from 0.5% to 5% by weight, more preferred from 0.5% to 3% by weight.

A number of other materials may optionally be added to the rinse-off compositions. Preferably they are present at levels from 0.1% to 2% by weight. Such materials include proteins and polypeptides and derivatives thereof; water-soluble or solubilizable preservatives such as DMDM Hydantoin®, Germall 115®, methyl-, ethyl-, propyl- and butyl esters of hydroxybenzoic acid, EDTA, Euxyl (RTM) K400; natural preservatives such as benzyl alcohol, potassium sorbate and bisabolol; sodium benzoate and 2-phenoxyethanol; moisturizing agents such as hyaluronic acid, chitin and starch-grafted sodium polyacrylates such as Sanwet® (RTM) IM-1000, IM-1500 and IM-2500 (Celanese Superabsorbent Materials, Portsmith, Va., USA, also described in U.S. Pat. No. 4,076,663); solvents; suitable anti-bacterial agents such as Oxeco (phenoxy isopropanol), Trichlorocarbanilide (TCC) and Triclosan, low temperature phase modifiers such as ammonium ion sources (e.g. $NH_4Cl$); viscosity control agents such as magnesium sulfate and other electrolytes; colouring agents; $TiO_2$ and $TiO_2$-coated mica; perfumes and perfume solubilizers; zeolites such as Valfour BV400 and derivatives thereof and $Ca^{2+}/Mg^{2+}$ sequestrants such as polycarboxylates, amino polycarboxylates, polyphosphonates, amino polyphosphonates and EDTA; water softening agents such as sodium citrate and insoluble particulates such as zinc stearate and fumed silica.

The rinse-off compositions preferably have a pH from 3 to 10, more preferred from 5 to 9, particularly preferred from 5 to 8, highly preferred from 5 to 7.

The rinse-off compositions can be used in a wide variety of skin and hair care compositions. Preferred compositions are shampoos, hair shampoos, conditioning shampoos, shower gels and body washes.

Surprisingly it has been found that the trimethylsilylalkylsilsesquioxane of formula (1) are particulary useful for formulating rinse-off compositions, preferably shampoos, which additionally contain insoluble components, preferably pearlescent and/or opacifying agents. Preferably the opacifier/pearlescer is present in the form of crystals. Compositions containing trimethylsilyloctylsilsesquioxanes (caprylyltrimethicones) and pearlizing or opacifying agents are stable over a long period of time and broad temperature ranges.

Preferred opacifiers and pearlescers include titanium dioxide; EUPERLAN 810® (RTM); TEGO-PEARL® (RTM); long chain ($C_{16}$–$C_{22}$) acyl derivatives such as glycol or polyethylene glycol esters of fatty acids having from 16 to 22 carbon atoms and up to 7 ethyleneoxide units; alkanolamides of fatty acids having from 16 to 22 carbon atoms, preferably from 16 to 18 carbon atoms, such as stearic monoethanolamide, stearic diethanolamide, stearic monoisopropanolamide, stearic monoethanolamide; alkyl-($C_{16}$–$C_{22}$) dimethyl oxides such as stearyl dimethyl amine oxide; polystyrene dispersions having a particle size from about 0.05 microns to about 0.45 microns, preferably from about 0.17 microns to about 0.3 microns (such dispersions are preferred in respect of the rheology and shear-thinning behaviour); styrene acrylate copolymers and OPACFIER 680® (RTM) (Morton International).

Preferred perlescent and opacifying agents are ethylene glycol esters of fatty acids having from 16 to 22 carbon atoms. More preferred are ethylene glycol stearates, both mono- and distearate.

Preferably the perlescent and opacifying agents are present at levels from 0.01% to 5% by weight, more preferred from 0.2% to 1.3% by weight.

In a preferred embodiment of the invention the compositions comprising perlescent and/or opacifying agents additionally comprise one or more suspending agents. Preferred suspending agents are those already described in the present application.

The rinse-off compositions of the present invention provide excellent rinse, feel and mildness benefits together with excellent rheological attributes in storage, in dispensing and in use. Moreover said products show good efficacy benefits, skin conditioning, skin moisturising, product stability, cleansing and lathering.

Subject-matter of the present invention is also a process for increasing the gloss and sheen of hair, wherein said process comprises applying an effective amount of a rinse-off composition comprising at least 0.1% by weight of at least one trimethyl-silylalkylsilsesquioxane of formula (1)

$$Me_3SiO\text{---}[Si(R)(OSiMe_3)O]_x\text{---}SiMe_3 \qquad (1)$$

wherein Me is methyl, R is a straight or branched alkyl group having from 6 to 18 carbon atoms and x is a number from 1 to 10, and at least 2% by weight of water-soluble surfactants, and at least 50% by weight of water to said hair.

In a further aspect the present invention provides processes for increasing the emolliency and increasing the water repellency of the skin, wherein said processes comprise applying an effective amount of a rinse-off composition comprising at least 0.1% by weight of at least one trimethyl-silylalkylsilsesquioxane of formula (1)

$$Me_3SiO\text{---}[Si(R)(OSiMe_3)O]_x\text{---}SiMe_3 \qquad (1)$$

wherein Me is methyl, R is a straight or branched alkyl group having from 6 to 18 carbon atoms and x is a number from 1 to 4, and wherein the the trimethyl-silylalkylsilsesquioxane is substantially free of alkoxysilanes, chlorosilanes, silanol functionalities and organic and/or inorganic compounds, at least 2% by weight of water-soluble surfactants and at least 50% by weight of water to said skin.

Trimethylsilylalkylsilsesquioxane of formula (1) which are preferred for use in the above three processes are those already described in the present application.

EXAMPLE

The compositions according to the present invention are illustrated by the following non-limiting examples.

Conditioning Shampoo 2-In-1

| Ingredients | % w/w | Trade name | Supplier |
| --- | --- | --- | --- |
| Phase A | | | |
| Deionized Water | Q.S. | N/A | N/A |
| Sodium Laureth (2) sulfate | 9.80 | Rhodapex ES-2 | Rhodia |
| Sodium Lauryl Sulfate | 13.60 | Rhodapon SB-8208/S | Rhodia |
| Cocoamidopropyl hydroxysultaine | 8.10 | Crosultaine C-50 | Croda |
| Cocamide MEA | 5.10 | Colamid CMA | Colonial |
| Polyquaternium-11 | 1.60 | Grafquat 734 | ISP |
| Steareth-2 | 0.90 | Brij 721 | Uniquema |
| Steareth-21 | 0.10 | Brij 72 | Uniquema |
| Caprylyl Trimethicone | 1.00 | Silcare 31M50 | Clariant |
| Panthenol | 1.00 | Panthenol | Jeen Int |
| Methylparaben | 0.20 | Nipagin M | NIPA |
| Propylparaben | 0.10 | Nipasol M | NIPA |
| Disodium EDTA | 0.10 | Dissolvine Na2 | Akzo |
| Phase B | | | |
| Fragrance | 0.30 | | |

Manufacturing Process

Heat the water of phase A up to 50 to 55° C.

While slowly mixing add the ingredients of phase A, one by one

Cool phase A down to 30–35° C.

Add phase B (fragrance), and mix until clear

What is claimed is:

1. A liquid rinse-off composition for personal care comprising
    a) at least 0.1% by weight of at least one trimethyl-silylalkylsilsesquioxane of formula (1)

$$Me_3SiO\text{---}[Si(R)(OSiMe_3)O]_x\text{---}SiMe_3 \quad (1)$$

wherein Me is methyl, R is a straight or branched alkyl group having from 6 to 18 carbon atoms and x is a number from 1 to 10,
    b) at least 2% by weight of water-soluble surfactants and
    c) at least 50% by weight of water.

2. The composition according to claim 1 wherein R in formula (1) has from 6 to 14 carbon atoms.

3. The composition according to claim 2 wherein R in formula (1) is an n-octyl group.

4. The composition according to claim 1 wherein x in formula (1) is a number from 1 to 6, preferably a number being equal to 1, 2 or 3.

5. The composition according to claim 1 wherein said trimethyl-silylalkylsilsesquioxanes of formula (1) are substantially free of alkoxysilanes, chlorosilanes, silanol functionalities and organic and/or inorganic compounds.

6. The composition according to claim 5, wherein said trimethylsilylalkylsilsesquioxanes of formula (1) contain less than 3% by weight, more preferred less than 1% by weight, of alkoxysilanes, chlorosilanes, silanol functionalities and organic and/or inorganic compounds.

7. The composition according to claim 1 which comprises from 0.1 to 5% by weight of trimethylsilylalkyl-silsesquioxanes of formula (1).

8. The composition according to claim 1 which comprises from 2 to 40% by weight of water-soluble surfactants.

9. The composition according to claim 1 which comprises from 50 to 90% by weight of water.

10. The composition according to claim 1 additionally comprising pearlescent agents and/or opacifying agents.

11. The composition according to claim 10 wherein said pearlescent agents or opacifying agents are ethylene glycol esters of ($C_{16}$–$C_{22}$) fatty acids.

12. The composition according to claim 11 wherein said pearlescent agents or opacifying agents are ethylene glycol stearates.

13. The composition according to claim 10, comprising from 0.01% to 5% by weight, more preferred from 0.2% to 1.3% by weight, of pearlescent agents and/or opacifying agents.

14. The composition according to claim 1 which is a shampoo, a shower gel or a body wash.

15. The composition according to claim 10 which is a shampoo.

16. The process for increasing the gloss and sheen of hair, wherein said process comprises applying an effective amount of a rinse-off composition comprising
    a) at least 0.1% by weight of at least one trimethylp-silylalkylsilsesquioxane of formula (1)

$$Me_3SiO\text{---}[Si(R)(OSiMe_3)O]_x\text{---}SiMe_3 \quad (1)$$

wherein Me is methyl, R is a straight or branched alkyl group having from 6 to 18 carbon atoms and x is a number from 1 to 10,
    b) at least 2% by weight of water soluble surfactants and
    c) at least 50% by weight of water to said hair.

* * * * *